United States Patent
Johnston et al.

(10) Patent No.: US 12,241,570 B2
(45) Date of Patent: Mar. 4, 2025

(54) NEGATIVE PRESSURE CONNECTOR SEAL

(71) Applicant: C. R. Bard, Inc., Franklin Lakes, NJ (US)

(72) Inventors: Gabriel A. Johnston, Broomfield, CO (US); Sean E. Walker, Platteville, CO (US); Madeline Stich, Thornton, CO (US); Brett R. Skelton, Louisville, CO (US); Karthik Ganesan, Longmont, CO (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 31 days.

(21) Appl. No.: 17/848,074

(22) Filed: Jun. 23, 2022

(65) Prior Publication Data

US 2023/0009524 A1    Jan. 12, 2023

Related U.S. Application Data

(60) Provisional application No. 63/219,247, filed on Jul. 7, 2021.

(51) Int. Cl.
| | | |
|---|---|---|
| *F16L 21/00* | (2006.01) | |
| *A61F 7/00* | (2006.01) | |
| *F16K 15/14* | (2006.01) | |

(52) U.S. Cl.
CPC ........... *F16L 21/005* (2013.01); *A61F 7/0085* (2013.01); *F16K 15/1471* (2021.08)

(58) Field of Classification Search
CPC . F16L 17/00; F16L 17/06; F16L 21/00; F16L 21/002; F16L 21/005; F16L 47/20;
(Continued)

(56) References Cited

U.S. PATENT DOCUMENTS 2,167,865 A * 8/1939 Beecher .............. F16L 21/005
                                                    285/133.11
2,250,325 A    7/1941 Barnes
(Continued)

FOREIGN PATENT DOCUMENTS

AU            678753 B3    6/1997
AU       2007201161 B2    12/2010
(Continued)

OTHER PUBLICATIONS

PCT/US2016/015688 filed Jan. 29, 2016 International Search Report and Written Opinion dated Apr. 1, 2016.
(Continued)

*Primary Examiner* — Aaron M Dunwoody
(74) *Attorney, Agent, or Firm* — Rutan & Tucker LLP

(57) ABSTRACT

A sealing member for providing a seal between fluid connectors includes a tubular member defining a lumen extending between a first end and a second end. The tubular member may receive a first connector via the first end and a second connector via the second end, and includes an annular wall extending between a first annular portion adjacent the first end and a second annular portion adjacent the second end. The first annular portion may engage the first connector, and the second annular portion may engage the second connector. When a pressure within the lumen is negative, atmospheric acting inward on the annular wall compresses the sealing member to define a contact force between the second annular portion and the second connector sufficient to define a fluid seal between the sealing member and the second connector.

24 Claims, 3 Drawing Sheets

(58) Field of Classification Search
CPC ......... F16L 47/22; F16L 47/24; F16L 55/168; F16L 55/17; F16L 55/1705; F16L 21/022; F16L 21/02; F16L 21/03; F16L 33/00; F16L 33/20; F16L 33/207; F16L 31/00
USPC .......................... 285/417, 418, 9.2, 235, 236
See application file for complete search history.

(56) References Cited

U.S. PATENT DOCUMENTS

| | | |
|---|---|---|
| 2,296,207 A | 9/1942 | Kittinger |
| 2,595,328 A | 5/1952 | Bowen |
| 2,602,302 A | 7/1952 | Poux |
| 2,726,658 A | 12/1955 | Chessey |
| 2,807,809 A | 10/1957 | Kottemann |
| 3,075,529 A | 1/1963 | Young, Jr. |
| 3,091,242 A | 5/1963 | Johnson, Jr. et al. |
| 3,212,286 A | 10/1965 | Curtis |
| 3,506,013 A | 4/1970 | Zdenek |
| 3,734,293 A | 5/1973 | Biskis |
| 3,830,676 A | 8/1974 | Elkins |
| 3,867,939 A | 2/1975 | Moore et al. |
| 3,900,035 A | 8/1975 | Welch et al. |
| 3,927,671 A | 12/1975 | Chittenden et al. |
| 3,945,617 A * | 3/1976 | Callery ............... B01F 35/71 215/DIG. 8 |
| 3,995,621 A | 12/1976 | Fletcher et al. |
| 4,059,293 A * | 11/1977 | Sipler ................. F16L 27/11 285/236 |
| 4,092,982 A | 6/1978 | Salem |
| 4,108,146 A | 8/1978 | Golden |
| 4,114,620 A | 9/1978 | Moore et al. |
| 4,118,946 A | 10/1978 | Tubin |
| 4,149,541 A | 4/1979 | Gammons et al. |
| 4,154,245 A | 5/1979 | Daily |
| 4,161,210 A | 7/1979 | Reid et al. |
| 4,195,631 A | 4/1980 | Baucom |
| 4,311,022 A | 1/1982 | Hall |
| 4,444,727 A | 4/1984 | Yanagihara et al. |
| 4,508,123 A | 4/1985 | Wyatt et al. |
| 4,580,408 A | 4/1986 | Stuebner |
| 4,753,241 A | 6/1988 | Brannigan et al. |
| 4,834,705 A | 5/1989 | Vaillancourt |
| 4,846,176 A | 7/1989 | Golden |
| 4,867,748 A | 9/1989 | Samuelsen |
| 4,884,304 A | 12/1989 | Elkins |
| 4,886,063 A | 12/1989 | Crews |
| 4,908,248 A | 3/1990 | Nakashima et al. |
| 4,919,134 A | 4/1990 | Streeter |
| 4,962,761 A | 10/1990 | Golden |
| 4,981,135 A | 1/1991 | Hardy |
| 4,989,607 A | 2/1991 | Keusch et al. |
| 5,000,252 A | 3/1991 | Faghri |
| 5,005,374 A | 4/1991 | Spitler |
| 5,050,596 A | 9/1991 | Walasek et al. |
| 5,062,414 A | 11/1991 | Grim |
| 5,072,875 A | 12/1991 | Zacoi |
| 5,090,409 A | 2/1992 | Genis |
| 5,097,829 A | 3/1992 | Quisenberry |
| 5,111,668 A | 5/1992 | Parrish et al. |
| 5,113,666 A | 5/1992 | Parrish et al. |
| 5,133,348 A | 7/1992 | Mayn |
| 5,146,625 A | 9/1992 | Steele et al. |
| 5,154,706 A | 10/1992 | Cartmell et al. |
| 5,190,032 A | 3/1993 | Zacoi |
| 5,265,669 A | 11/1993 | Schneider |
| 5,268,022 A | 12/1993 | Garrett et al. |
| 5,289,695 A | 3/1994 | Parrish et al. |
| 5,300,103 A | 4/1994 | Stempel et al. |
| 5,304,213 A | 4/1994 | Berke et al. |
| 5,304,216 A | 4/1994 | Wallace |
| 5,320,164 A | 6/1994 | Szczesuil et al. |
| 5,383,919 A | 1/1995 | Kelly et al. |
| 5,393,462 A | 2/1995 | Avery |
| 5,405,366 A | 4/1995 | Fox et al. |
| 5,407,421 A | 4/1995 | Goldsmith |
| 5,409,500 A | 4/1995 | Dyrek |
| 5,411,541 A | 5/1995 | Bell et al. |
| 5,423,751 A | 6/1995 | Harrison et al. |
| 5,456,701 A | 10/1995 | Stout |
| 5,466,250 A | 11/1995 | Johnson, Jr. et al. |
| 5,470,353 A | 11/1995 | Jensen |
| 5,476,489 A | 12/1995 | Koewler |
| 5,484,448 A | 1/1996 | Steele et al. |
| 5,486,207 A | 1/1996 | Mahawili |
| 5,514,169 A | 5/1996 | Dickerhoff et al. |
| 5,545,194 A | 8/1996 | Augustine |
| 5,605,144 A | 2/1997 | Simmons et al. |
| 5,609,620 A | 3/1997 | Daily |
| 5,620,482 A | 4/1997 | Augustine et al. |
| 5,624,477 A | 4/1997 | Armond |
| 5,634,940 A | 6/1997 | Panyard |
| 5,640,728 A | 6/1997 | Graebe |
| 5,645,855 A | 7/1997 | Lorenz |
| 5,658,325 A | 8/1997 | Augustine |
| 5,662,695 A | 9/1997 | Mason et al. |
| 5,683,439 A | 11/1997 | Jensen |
| 5,720,774 A | 2/1998 | Glucksman |
| 5,733,318 A | 3/1998 | Augustine |
| 5,755,755 A | 5/1998 | Panyard |
| 5,785,716 A | 7/1998 | Bayron et al. |
| 5,806,335 A | 9/1998 | Herbert et al. |
| 5,824,025 A | 10/1998 | Augustine |
| 5,837,002 A | 11/1998 | Augustine et al. |
| 5,840,080 A | 11/1998 | Der Ovanesian |
| 5,843,145 A | 12/1998 | Brink |
| 5,871,526 A | 2/1999 | Gibbs et al. |
| 5,879,378 A | 3/1999 | Usui |
| 5,887,437 A | 3/1999 | Maxim |
| 5,913,849 A | 6/1999 | Sundstrom et al. |
| 5,948,012 A | 9/1999 | Mahaffey et al. |
| 5,968,000 A | 10/1999 | Harrison et al. |
| 5,986,163 A | 11/1999 | Augustine |
| 5,989,285 A | 11/1999 | DeVilbiss et al. |
| 6,010,528 A | 1/2000 | Augustine et al. |
| 6,019,783 A | 2/2000 | Philips et al. |
| 6,030,412 A | 2/2000 | Klatz et al. |
| 6,047,106 A | 4/2000 | Salyer |
| 6,074,415 A | 6/2000 | Der Ovanesian |
| 6,083,256 A | 7/2000 | Der Ovanesian |
| 6,083,418 A | 7/2000 | Czarnecki et al. |
| 6,117,164 A | 9/2000 | Gildersleeve et al. |
| 6,176,869 B1 | 1/2001 | Mason et al. |
| 6,176,870 B1 | 1/2001 | Augustine |
| 6,185,744 B1 | 2/2001 | Poholski |
| 6,188,930 B1 | 2/2001 | Carson |
| 6,189,149 B1 | 2/2001 | Allen |
| 6,189,550 B1 * | 2/2001 | Stickel ............... F16L 27/1021 285/236 |
| 6,197,045 B1 | 3/2001 | Carson |
| 6,234,538 B1 | 5/2001 | Lauer |
| 6,238,427 B1 | 5/2001 | Matta |
| 6,255,552 B1 | 7/2001 | Cummings et al. |
| 6,257,011 B1 | 7/2001 | Siman-Tov et al. |
| 6,290,716 B1 | 9/2001 | Augustine |
| 6,336,935 B1 | 1/2002 | Davis et al. |
| 6,349,560 B1 | 2/2002 | Maier-Laxhuber et al. |
| 6,352,550 B1 | 3/2002 | Gildersleeve et al. |
| 6,364,937 B1 | 4/2002 | McMahon |
| 6,371,976 B1 | 4/2002 | Vrzalik et al. |
| 6,375,674 B1 | 4/2002 | Carson |
| 6,389,839 B1 | 5/2002 | Sabin |
| 6,436,130 B1 | 8/2002 | Philips et al. |
| 6,454,792 B1 | 9/2002 | Noda et al. |
| 6,461,379 B1 | 10/2002 | Carson et al. |
| 6,463,212 B1 | 10/2002 | Salyer |
| 6,503,297 B1 | 1/2003 | Lu et al. |
| 6,508,831 B1 | 1/2003 | Kushnir |
| 6,508,859 B1 | 1/2003 | Zia et al. |
| 6,511,501 B1 | 1/2003 | Augustine et al. |
| 6,511,502 B2 | 1/2003 | Fletcher |
| 6,517,510 B1 | 2/2003 | Stewart et al. |
| D471,987 S | 3/2003 | Hoglund et al. |
| D472,322 S | 3/2003 | Hoglund et al. |
| D474,544 S | 5/2003 | Hoglund et al. |

(56) References Cited

U.S. PATENT DOCUMENTS

| | | |
|---|---|---|
| 6,559,096 B1 | 5/2003 | Smith et al. |
| 6,584,797 B1 | 7/2003 | Smith et al. |
| 6,591,630 B2 | 7/2003 | Smith et al. |
| 6,601,404 B1 | 8/2003 | Roderick |
| 6,613,030 B1 | 9/2003 | Coles et al. |
| 6,620,187 B2 | 9/2003 | Carson et al. |
| 6,620,188 B1 | 9/2003 | Ginsburg et al. |
| 6,645,232 B2 | 11/2003 | Carson |
| 6,648,905 B2 | 11/2003 | Hoglund et al. |
| 6,653,607 B2 | 11/2003 | Ellis et al. |
| D483,125 S | 12/2003 | Hoglund et al. |
| 6,660,027 B2 | 12/2003 | Gruszecki et al. |
| 6,669,715 B2 | 12/2003 | Hoglund et al. |
| 6,682,525 B2 | 1/2004 | Lalonde et al. |
| D487,147 S | 2/2004 | Ellingboe et al. |
| D487,148 S | 2/2004 | Ellingboe et al. |
| 6,688,132 B2 | 2/2004 | Smith et al. |
| 6,692,518 B2 | 2/2004 | Carson |
| 6,699,267 B2 | 3/2004 | Voorhees et al. |
| 6,701,724 B2 | 3/2004 | Smith et al. |
| 6,743,250 B2 | 6/2004 | Renfro |
| 6,755,801 B2 | 6/2004 | Utterberg et al. |
| 6,755,852 B2 | 6/2004 | Lachenbruch et al. |
| D492,773 S | 7/2004 | Ellingboe et al. |
| 6,770,848 B2 | 8/2004 | Haas et al. |
| 6,799,063 B2 | 9/2004 | Carson |
| 6,800,087 B2 | 10/2004 | Papay et al. |
| 6,802,855 B2 | 10/2004 | Ellingboe et al. |
| 6,802,885 B2 | 10/2004 | Luk et al. |
| 6,818,012 B2 | 11/2004 | Ellingboe |
| 6,827,728 B2 | 12/2004 | Ellingboe et al. |
| 6,846,322 B2 | 1/2005 | Kane et al. |
| 6,858,068 B2 | 2/2005 | Smith et al. |
| 6,878,156 B1 | 4/2005 | Noda |
| 6,893,453 B2 | 5/2005 | Agarwal et al. |
| 6,904,956 B2 | 6/2005 | Noel |
| 6,909,074 B1 | 6/2005 | Bradley |
| 6,921,198 B2 | 7/2005 | Gruszecki et al. |
| 6,931,875 B1 | 8/2005 | Allen et al. |
| 6,942,644 B2 | 9/2005 | Worthen |
| 6,960,243 B1 | 11/2005 | Smith et al. |
| 6,968,711 B2 | 11/2005 | Smith et al. |
| 6,969,399 B2 | 11/2005 | Schock et al. |
| 7,008,445 B2 | 3/2006 | Lennox |
| 7,022,099 B2 | 4/2006 | Litzie et al. |
| 7,044,960 B2 | 5/2006 | Voorhees et al. |
| 7,052,509 B2 | 5/2006 | Lennox et al. |
| 7,055,575 B2 | 6/2006 | Noel |
| 7,056,335 B2 | 6/2006 | Agarwal et al. |
| 7,063,718 B2 | 6/2006 | Dobak, III |
| 7,077,858 B2 | 7/2006 | Fletcher et al. |
| 7,097,657 B2 | 8/2006 | Noda et al. |
| 7,101,389 B1 | 9/2006 | Augustine et al. |
| 7,122,047 B2 | 10/2006 | Grahn et al. |
| 7,160,316 B2 | 1/2007 | Hamilton et al. |
| 7,172,586 B1 | 2/2007 | Dae et al. |
| 7,240,720 B2 | 7/2007 | Noel |
| 7,303,554 B2 | 12/2007 | Alonde et al. |
| 7,303,579 B2 | 12/2007 | Schock et al. |
| 7,338,516 B2 | 3/2008 | Quincy, III et al. |
| 7,361,186 B2 | 4/2008 | Voorhees et al. |
| 7,377,935 B2 | 5/2008 | Schock et al. |
| 7,507,250 B2 | 3/2009 | Lennox |
| 7,517,360 B2 | 4/2009 | Frey et al. |
| RE40,815 E | 6/2009 | Kudaravalli et al. |
| 7,547,320 B2 | 6/2009 | Schook et al. |
| RE40,868 E | 8/2009 | Ryba et al. |
| 7,621,944 B2 | 11/2009 | Wilson et al. |
| 7,621,945 B2 | 11/2009 | Lennox et al. |
| 7,666,213 B2 | 2/2010 | Freedman, Jr. et al. |
| 7,678,716 B2 | 3/2010 | Yahiaoui et al. |
| 7,686,840 B2 | 3/2010 | Quincy, III et al. |
| 7,727,228 B2 | 6/2010 | Abboud et al. |
| 7,731,739 B2 | 6/2010 | Schock et al. |
| 7,744,640 B1 | 6/2010 | Faries, Jr. et al. |
| 7,749,261 B2 | 7/2010 | Hansen et al. |
| 7,763,061 B2 | 7/2010 | Schorr et al. |
| 7,771,461 B2 | 8/2010 | Schock et al. |
| 7,784,304 B2 | 8/2010 | Trinh et al. |
| 7,799,063 B2 | 9/2010 | Ingram et al. |
| 7,827,815 B2 | 11/2010 | Carson et al. |
| 7,867,266 B2 | 1/2011 | Collins |
| 7,892,269 B2 | 2/2011 | Collins et al. |
| 7,896,910 B2 | 3/2011 | Schirrmacher et al. |
| 7,918,243 B2 | 4/2011 | Diodati et al. |
| 8,047,010 B2 | 11/2011 | Carson et al. |
| 8,052,624 B2 | 11/2011 | Buchanan et al. |
| 8,066,752 B2 | 11/2011 | Hamilton et al. |
| 8,182,521 B2 | 5/2012 | Kane et al. |
| 8,187,697 B2 | 5/2012 | Quincy, III et al. |
| 8,283,602 B2 | 10/2012 | Augustine et al. |
| 8,454,671 B2 | 6/2013 | Lennox et al. |
| D685,916 S | 7/2013 | Hoglund |
| 8,491,644 B1 | 7/2013 | Carson et al. |
| 8,597,217 B2 | 12/2013 | Lowe et al. |
| 8,597,339 B2 | 12/2013 | Augustine et al. |
| 8,603,150 B2 | 12/2013 | Kane et al. |
| 8,632,576 B2 | 1/2014 | Quisenberry |
| 8,647,374 B2 | 2/2014 | Koewler |
| 8,715,330 B2 | 5/2014 | Lowe et al. |
| 8,778,119 B2 | 7/2014 | Starr et al. |
| 8,808,344 B2 | 8/2014 | Scott et al. |
| 8,840,581 B2 | 9/2014 | McGill et al. |
| 9,034,458 B2 | 5/2015 | Li |
| 9,078,742 B2 | 7/2015 | Quincy, III et al. |
| 9,089,462 B1 | 7/2015 | Lafleche |
| 9,211,358 B2 | 12/2015 | Sinko et al. |
| 9,278,024 B2 | 3/2016 | Scott et al. |
| 9,333,112 B2 | 5/2016 | Carson |
| 9,552,706 B2 | 1/2017 | Schneider et al. |
| 9,566,185 B2 | 2/2017 | Carson et al. |
| 9,622,907 B2 | 4/2017 | Carson et al. |
| 9,687,386 B2 | 6/2017 | Carson |
| 9,763,823 B2 | 9/2017 | Voorhees et al. |
| 9,907,889 B2 | 3/2018 | Locke et al. |
| 10,010,452 B2 | 7/2018 | Wenske et al. |
| 10,123,902 B2 | 11/2018 | Carson et al. |
| 10,220,198 B2 | 3/2019 | Fuchs et al. |
| 10,258,501 B2 | 4/2019 | Carson |
| 10,441,458 B2 | 10/2019 | Voorhees et al. |
| 10,441,707 B2 | 10/2019 | Voorhees et al. |
| 10,548,778 B2 | 2/2020 | Hassenpflug et al. |
| 10,912,672 B1 | 2/2021 | Jones et al. |
| 11,234,859 B2 | 2/2022 | Voorhees et al. |
| 11,285,039 B2 | 3/2022 | Steele et al. |
| 11,975,123 B2 | 5/2024 | Appel et al. |
| 2001/0039439 A1 | 11/2001 | Elkins et al. |
| 2002/0007203 A1 | 1/2002 | Gilmartin et al. |
| 2002/0015689 A1 | 2/2002 | Munro et al. |
| 2002/0111657 A1 | 8/2002 | Dae et al. |
| 2002/0138121 A1 | 9/2002 | Fox |
| 2002/0161419 A1 | 10/2002 | Carson et al. |
| 2003/0074038 A1 | 4/2003 | Gruszecki et al. |
| 2003/0078638 A1 | 4/2003 | Voorhees et al. |
| 2003/0078639 A1 | 4/2003 | Carson |
| 2003/0078640 A1 | 4/2003 | Carson et al. |
| 2003/0109911 A1 | 6/2003 | Lachenbruch et al. |
| 2003/0114903 A1 | 6/2003 | Ellingboe |
| 2003/0135252 A1 | 7/2003 | MacHold et al. |
| 2003/0149359 A1 | 8/2003 | Smith |
| 2003/0149461 A1 | 8/2003 | Johnson |
| 2003/0150232 A1 | 8/2003 | Brudnicki |
| 2003/0163179 A1 | 8/2003 | Hoglund et al. |
| 2003/0163180 A1 | 8/2003 | Hoglund et al. |
| 2003/0163183 A1 | 8/2003 | Carson |
| 2003/0163185 A1 | 8/2003 | Carson |
| 2003/0212416 A1 | 11/2003 | Cinelli et al. |
| 2004/0030372 A1 | 2/2004 | Ellingboe et al. |
| 2004/0030373 A1 | 2/2004 | Ellingboe et al. |
| 2004/0059212 A1 | 3/2004 | Abreu |
| 2004/0064170 A1 | 4/2004 | Radons et al. |
| 2004/0073280 A1 | 4/2004 | Dae et al. |
| 2004/0082886 A1 | 4/2004 | Timpson |
| 2004/0087606 A1 | 5/2004 | Voorhees et al. |

(56) References Cited

U.S. PATENT DOCUMENTS

| | | |
|---|---|---|
| 2004/0133253 A1 | 7/2004 | Grahn et al. |
| 2004/0225341 A1 | 11/2004 | Schock et al. |
| 2004/0243122 A1 | 12/2004 | Auth et al. |
| 2004/0252750 A1 | 12/2004 | Gruszecki et al. |
| 2004/0260369 A1 | 12/2004 | Schock et al. |
| 2004/0267339 A1 | 12/2004 | Yon et al. |
| 2005/0028551 A1 | 2/2005 | Noda et al. |
| 2005/0060012 A1 | 3/2005 | Voorhees et al. |
| 2005/0065583 A1 | 3/2005 | Voorhees et al. |
| 2005/0096714 A1 | 5/2005 | Freedman et al. |
| 2005/0177212 A1 | 8/2005 | Njemanze |
| 2005/0187502 A1 | 8/2005 | Krempel et al. |
| 2005/0244629 A1 | 11/2005 | Usui et al. |
| 2005/0288749 A1 | 12/2005 | Lachenbruch |
| 2006/0024053 A1 | 2/2006 | Grant |
| 2006/0030916 A1 | 2/2006 | Lennox |
| 2006/0036304 A1 | 2/2006 | Cordani et al. |
| 2006/0058858 A1 | 3/2006 | Smith |
| 2006/0074469 A1 | 4/2006 | Lennox et al. |
| 2006/0122673 A1 | 6/2006 | Callister et al. |
| 2006/0124141 A1 | 6/2006 | Dobak |
| 2006/0136023 A1 | 6/2006 | Dobak |
| 2006/0161232 A1 | 7/2006 | Kasza et al. |
| 2006/0190066 A1 | 8/2006 | Worthen |
| 2006/0235114 A1 | 10/2006 | Kitazono et al. |
| 2006/0247744 A1 | 11/2006 | Nest et al. |
| 2006/0276089 A1 | 12/2006 | Amarasinghe et al. |
| 2006/0287697 A1 | 12/2006 | Lennox |
| 2006/0293734 A1 | 12/2006 | Scott et al. |
| 2007/0043409 A1 | 2/2007 | Brian et al. |
| 2007/0049997 A1 | 3/2007 | Fields et al. |
| 2007/0054122 A1 | 3/2007 | Paisner et al. |
| 2007/0068931 A1 | 3/2007 | Augustine et al. |
| 2007/0100404 A1 | 5/2007 | Ko et al. |
| 2007/0173735 A1 | 7/2007 | Callister et al. |
| 2007/0213793 A1 | 9/2007 | Hayes |
| 2007/0225782 A1 | 9/2007 | Taylor |
| 2007/0244475 A1 | 10/2007 | Carson et al. |
| 2007/0270925 A1 | 11/2007 | Levinson |
| 2008/0027523 A1 | 1/2008 | Behringer et al. |
| 2008/0046046 A1 | 2/2008 | Ginsburg |
| 2008/0114431 A1 | 5/2008 | Ginsburg |
| 2008/0147152 A1 | 6/2008 | Quincy et al. |
| 2008/0249524 A1 | 10/2008 | Dunning |
| 2008/0255644 A1 | 10/2008 | Carson |
| 2008/0275534 A1 | 11/2008 | Noel |
| 2009/0018504 A1 | 1/2009 | Pile-Spellman et al. |
| 2009/0043366 A1 | 2/2009 | Dae |
| 2009/0066079 A1 | 3/2009 | Miros et al. |
| 2009/0088825 A1 | 4/2009 | Ota |
| 2009/0099629 A1 | 4/2009 | Carson et al. |
| 2009/0131835 A1 | 5/2009 | Voorhees et al. |
| 2009/0157000 A1 | 6/2009 | Waller |
| 2009/0177184 A1 | 7/2009 | Christensen et al. |
| 2009/0182400 A1 | 7/2009 | Dae et al. |
| 2009/0250367 A1 | 10/2009 | Murdoch et al. |
| 2009/0280182 A1 | 11/2009 | Beck et al. |
| 2009/0287283 A1 | 11/2009 | Biser et al. |
| 2009/0299287 A1 | 12/2009 | Carson et al. |
| 2009/0312823 A1 | 12/2009 | Patience et al. |
| 2009/0326619 A1 | 12/2009 | Kagan |
| 2010/0016933 A1 | 1/2010 | Chen et al. |
| 2010/0168825 A1 | 7/2010 | Barbknecht |
| 2010/0198122 A1 | 8/2010 | Freund |
| 2010/0198320 A1 | 8/2010 | Pierre et al. |
| 2010/0204765 A1 | 8/2010 | Hall et al. |
| 2010/0312202 A1 | 12/2010 | Henley et al. |
| 2011/0021960 A1 | 1/2011 | Filtvedt et al. |
| 2011/0029051 A1 | 2/2011 | Ross |
| 2011/0045056 A1 | 2/2011 | Munro et al. |
| 2011/0125238 A1 | 5/2011 | Nofzinger |
| 2011/0152982 A1 | 6/2011 | Richardson |
| 2011/0166633 A1 | 7/2011 | Stull |
| 2011/0172749 A1 | 7/2011 | Christensen et al. |
| 2011/0306972 A1 | 12/2011 | Widenhouse et al. |
| 2011/0307040 A1 | 12/2011 | Peterson |
| 2011/0308781 A1 | 12/2011 | O'Riordan et al. |
| 2011/0313497 A1 | 12/2011 | McFarlane |
| 2012/0046720 A1 | 2/2012 | Ishizaki |
| 2012/0065715 A1 | 3/2012 | Carson |
| 2012/0080031 A1 | 4/2012 | Belson |
| 2012/0095536 A1 | 4/2012 | Machold et al. |
| 2012/0185021 A1 | 7/2012 | Johnson et al. |
| 2012/0191035 A1 | 7/2012 | Stephan |
| 2012/0220960 A1 | 8/2012 | Ruland |
| 2013/0023808 A1 | 1/2013 | Brown et al. |
| 2013/0116760 A1 | 5/2013 | Carson et al. |
| 2013/0238042 A1 | 9/2013 | Gildersleeve et al. |
| 2013/0310725 A1 | 11/2013 | Jerrells et al. |
| 2014/0039451 A1 | 2/2014 | Bangera et al. |
| 2014/0046411 A1 | 2/2014 | Elkins et al. |
| 2014/0172050 A1 | 6/2014 | Dabrowiak |
| 2014/0214138 A1 | 7/2014 | Voorhees et al. |
| 2014/0222121 A1 | 8/2014 | Spence et al. |
| 2014/0277301 A1 | 9/2014 | Varga et al. |
| 2014/0288621 A1 | 9/2014 | Efremkin |
| 2014/0316494 A1 | 10/2014 | Augustine et al. |
| 2014/0343639 A1 | 11/2014 | Hopper et al. |
| 2015/0051673 A1 | 2/2015 | Rivas Tapia |
| 2015/0223972 A1 | 8/2015 | Dabrowiak |
| 2015/0230973 A1 | 8/2015 | Dabrowiak et al. |
| 2015/0250643 A1 | 9/2015 | Paradis |
| 2015/0290042 A1 | 10/2015 | Freer et al. |
| 2015/0366703 A1 | 12/2015 | Du |
| 2015/0373781 A1 | 12/2015 | Augustine et al. |
| 2016/0008166 A1 | 1/2016 | Voorhees et al. |
| 2016/0022477 A1 | 1/2016 | Schaefer et al. |
| 2016/0038336 A1 | 2/2016 | Hilton et al. |
| 2016/0324683 A1 | 11/2016 | Carson |
| 2017/0049618 A1 | 2/2017 | Ward et al. |
| 2017/0135855 A1 | 5/2017 | Stefan et al. |
| 2017/0151087 A1 | 6/2017 | Carson et al. |
| 2017/0189225 A1 | 7/2017 | Voorhees et al. |
| 2017/0224528 A1 | 8/2017 | Berg et al. |
| 2017/0246029 A1 | 8/2017 | Clark |
| 2017/0246031 A1 | 8/2017 | Benyaminpour et al. |
| 2017/0246374 A1 | 8/2017 | Voorhees et al. |
| 2017/0348144 A1 | 12/2017 | Taylor et al. |
| 2017/0348145 A1 | 12/2017 | Voorhees et al. |
| 2017/0354534 A1 | 12/2017 | Paradis et al. |
| 2018/0042762 A1 | 2/2018 | Galer |
| 2018/0042763 A1 | 2/2018 | Galer et al. |
| 2018/0207024 A1 | 7/2018 | Dabrowiak et al. |
| 2018/0214297 A1 | 8/2018 | Hughett et al. |
| 2018/0214302 A1 | 8/2018 | Dabrowiak et al. |
| 2018/0263677 A1 | 9/2018 | Hilton et al. |
| 2018/0376539 A1 | 12/2018 | Augustine et al. |
| 2019/0083322 A1 | 3/2019 | Huang et al. |
| 2019/0085644 A1 | 3/2019 | Ames et al. |
| 2019/0117446 A1 | 4/2019 | Carson et al. |
| 2019/0192337 A1 | 6/2019 | Taylor et al. |
| 2019/0201574 A1 | 7/2019 | Delury et al. |
| 2019/0262169 A1 | 8/2019 | Vergara et al. |
| 2019/0331277 A1* | 10/2019 | Vachon .................. F16L 47/06 |
| 2020/0001022 A1 | 1/2020 | Landy, III et al. |
| 2020/0071051 A1 | 3/2020 | Lewis |
| 2020/0155341 A1 | 5/2020 | Voorhees et al. |
| 2020/0345971 A1 | 11/2020 | Schirm et al. |
| 2020/0405530 A1 | 12/2020 | Taylor et al. |
| 2021/0060230 A1 | 3/2021 | Hopper et al. |
| 2022/0087874 A1 | 3/2022 | Schneider et al. |
| 2022/0151821 A1 | 5/2022 | Voorhees et al. |
| 2022/0192865 A1 | 6/2022 | Hughett, Sr. et al. |
| 2022/0192867 A1 | 6/2022 | Stich et al. |
| 2022/0233344 A1 | 7/2022 | Hoglund |
| 2022/0233347 A1 | 7/2022 | Canary et al. |
| 2022/0265468 A1 | 8/2022 | Xu et al. |
| 2022/0280336 A1 | 9/2022 | Smith et al. |
| 2022/0287875 A1 | 9/2022 | Minchew et al. |
| 2022/0287876 A1 | 9/2022 | Smith et al. |
| 2022/0296413 A1 | 9/2022 | Jones |
| 2022/0296414 A1 | 9/2022 | Bible et al. |
| 2022/0304847 A1 | 9/2022 | Kuroda et al. |
| 2022/0313478 A1 | 10/2022 | Johnston |

(56) References Cited

U.S. PATENT DOCUMENTS

| | | | |
|---|---|---|---|
| 2022/0347009 | A1 | 11/2022 | Hughett, Sr. et al. |
| 2022/0401259 | A1 | 12/2022 | Basciano et al. |
| 2023/0000668 | A1 | 1/2023 | Walker et al. |
| 2023/0011631 | A1 | 1/2023 | Yin et al. |
| 2023/0019048 | A1 | 1/2023 | Stich et al. |
| 2023/0021245 | A1 | 1/2023 | Walker et al. |
| 2023/0040583 | A1 | 2/2023 | Falis et al. |
| 2023/0077318 | A9 | 3/2023 | Voorhees et al. |
| 2023/0190519 | A1 | 6/2023 | Stich et al. |
| 2024/0065884 | A1 | 2/2024 | Fallows et al. |
| 2024/0082052 | A1 | 3/2024 | Cho et al. |
| 2024/0091054 | A1 | 3/2024 | Boone-Worthman et al. |
| 2024/0099878 | A1 | 3/2024 | Voorhees et al. |
| 2024/0108497 | A1 | 4/2024 | Daw et al. |
| 2024/0366422 | A1 | 11/2024 | Johnston et al. |

FOREIGN PATENT DOCUMENTS

| | | | |
|---|---|---|---|
| CA | 2729122 | A1 | 7/2002 |
| CN | 102026596 | A | 4/2011 |
| CN | 101389372 | B | 8/2012 |
| CN | 102746518 | A | 10/2012 |
| CN | 103939695 | B | 3/2016 |
| CN | 113230017 | A | 8/2021 |
| DE | 102014118510 | A1 | 6/2016 |
| EP | 1073388 | A1 | 2/2001 |
| EP | 1616543 | A2 | 1/2006 |
| EP | 1641503 | A2 | 4/2006 |
| EP | 1718894 | B1 | 7/2010 |
| EP | 2204150 | A1 | 7/2010 |
| EP | 2269546 | A1 | 1/2011 |
| JP | 2007029638 | A | 2/2007 |
| JP | 2013248293 | A | 12/2013 |
| KR | 20110020420 | A | 3/2011 |
| WO | 9807397 | A1 | 2/1998 |
| WO | 98/31310 | A1 | 7/1998 |
| WO | 199944552 | A1 | 9/1999 |
| WO | 9953874 | A1 | 10/1999 |
| WO | 2000040185 | A1 | 7/2000 |
| WO | 2003086253 | A2 | 10/2003 |
| WO | 2004075949 | A2 | 9/2004 |
| WO | 2005028984 | A1 | 3/2005 |
| WO | 2005117546 | A2 | 12/2005 |
| WO | 2007120677 | A2 | 10/2007 |
| WO | 2009/090403 | A1 | 7/2009 |
| WO | 2009147413 | A1 | 12/2009 |
| WO | 2009148636 | A1 | 12/2009 |
| WO | 2012125916 | A2 | 9/2012 |
| WO | 2012138980 | A2 | 10/2012 |
| WO | 2016057119 | A1 | 4/2016 |
| WO | 2017/127768 | A1 | 7/2017 |
| WO | 2018075576 | A1 | 4/2018 |
| WO | 2022/159879 | A1 | 7/2022 |
| WO | 2022155130 | A1 | 7/2022 |
| WO | 2022155132 | A1 | 7/2022 |
| WO | 2022159513 | A1 | 7/2022 |
| WO | 2022/165068 | A1 | 8/2022 |
| WO | 2022235513 | A1 | 11/2022 |
| WO | 2023121674 | A1 | 6/2023 |
| WO | 2023140870 | A1 | 7/2023 |
| WO | 2023154050 | A1 | 8/2023 |

OTHER PUBLICATIONS

PCT/US2022/013672 filed Jan. 25, 2022, International Search Report and Written Opinion dated Jul. 15, 2022.
PCT/US2022/014147 filed Jan. 27, 2022 International Search Report and Written Opinion dated Jul. 18, 2022.
Advantage Engineering, "Proper Use of Inhibited Propylene Glycol", Jun. 12, 2001, http://www.ttequip.com/knowledgelibrary/Proper%20Use%20Of%20Inh- ibited%20Propylene%20Glycol.pdf Jun. 12, 2001.
Hyperphysicis, "Thermal Conductivity", available Jul. 31, 2010, https://web.archive.org/web/20100731025127/http://hyperphysics.phy-astr.g-us.edu/hbase/tables.thron.html Jul. 31, 2010.
Murray, R. Z., et al. "Development and use of biomaterials as wound healing therapies" Burns & Trauma (2019) 7:2 https://doi.org/10.1186/s41038-018-0139-7 (2019).
PCT/US2015/045548 filed Aug. 17, 2015 International Search Report and Written Opinion dated Nov. 24, 2015.
Sevgi, M., et al. "Topical Antimicrobials for Burn Infections—An Update" Recent Pat Antiinfect Drug Discov. Dec. 2013 ; 8(3): 161-197.
Stoica, A. E., et al. "Hydrogel Dressings for the Treatment of Burn Wounds: An Up-To-Date Overview" Materials 2020, 13, 2853; doi:10.3390/ma13122853. (2020).
U.S. Appl. No. 15/512,025, filed Mar. 16, 2017 Final Office Action dated Jun. 25, 2020.
U.S. Appl. No. 15/512,025, filed Mar. 16, 2017 Non-Final Office Action dated Jul. 18, 2019.
U.S. Appl. No. 16/597,393, filed Oct. 9, 2019 Corrected Notice of Allowability dated Nov. 18, 2021.
U.S. Appl. No. 16/597,393, filed Oct. 9, 2019 Non-Final Office Action dated Apr. 28, 2021.
PCT/US2022/011980 filed Jan. 11, 2022 International Search Report and Written Opinion dated Apr. 13, 2022.
PCT/US2022/013007 filed Jan. 19, 2022 International Search Report and Written Opinion dated Apr. 22, 2022.
PCT/US2022/026999 filed Apr. 29, 2022 International Search Report and Written Opinion dated Oct. 24, 2022.
PCTUS2022011971 filed Jan. 11, 2022 International Search Report and Written Opinion dated Apr. 21, 2022.
U.S. Appl. No. 17/589,849, filed Jan. 31, 2022 Final Office Action dated Jun. 27, 2023.
U.S. Appl. No. 17/589,849, filed Jan. 31, 2022 Non-Final Office Action dated Apr. 12, 2023.
U.S. Appl. No. 17/589,849, filed Jan. 31, 2022 Notice of Allowance dated Aug. 23, 2023.
PCT/US2021/065144 filed Dec. 23, 2021 International Search Report dated Oct. 4, 2022.
U.S. Appl. No. 18/536,087, filed Dec. 11, 2023 Non-Final Office Action dated Jun. 28, 2024.
PCT/US2022/013569 filed Jan. 24, 2022 International Search Report and Written Opinion dated Aug. 29, 2022.
PCT/US2022/016020 filed Feb. 10, 2022 International Search Report and Written Opinion dated Oct. 31, 2022.
U.S. Appl. No. 17/547,128, filed Dec. 9, 2021 Restriction Requirement dated Sep. 5, 2024.
U.S. Appl. No. 17/583,090, filed Jan. 24, 2022 Restriction Requirement dated Sep. 6, 2024.
U.S. Appl. No. 17/584,101, filed Jan. 25, 2022 Restriction Requirement dated Nov. 5, 2024.
U.S. Appl. No. 17/686,301, filed Mar. 3, 2022 Non-Final Office Action dated Oct. 1, 2024.
U.S. Appl. No. 17/689,791, filed Mar. 8, 2022 Restriction Requirement dated Oct. 16, 2024.
U.S. Appl. No. 17/691,990, filed Mar. 10, 2022 Restriction Requirement dated Oct. 16, 2024.
U.S. Appl. No. 17/694,416, filed Mar. 14, 2022 Restriction Requirement dated Nov. 8, 2024.
U.S. Appl. No. 17/709,019, filed Mar. 30, 2022 Restriction Requirement dated Oct. 16, 2024.
U.S. Appl. No. 17/723,210, filed Apr. 18, 2022 Restriction Requirement dated Oct. 16, 2024.
U.S. Appl. No. 17/849,419, filed Jun. 24, 2022 Non-Final Office Action dated Nov. 8, 2024.
U.S. Appl. No. 18/536,087, filed Dec. 11, 2023 Notice of Allowance dated Aug. 29, 2024.
U.S. Appl. No. 17/552,309, filed Dec. 15, 2021 Restriction Requirement dated Dec. 12, 2024.
U.S. Appl. No. 17/689,791, filed Mar. 8, 2022 Non-Final Office Action dated Dec. 30, 2024.
U.S. Appl. No. 17/690,908, filed Mar. 9, 2022 Non-Final Office Action dated Dec. 18, 2024.
U.S. Appl. No. 17/691,990, filed Mar. 10, 2022 Non-Final Office Action dated Dec. 17, 2024.

(56) References Cited

OTHER PUBLICATIONS

U.S. Appl. No. 17/709,019, filed Mar. 30, 2022 Non-Final Office Action dated Dec. 31, 2024.
U.S. Appl. No. 17/723,210, filed Apr. 18, 2022 Non-Final Office Action dated Dec. 20, 2024.

* cited by examiner

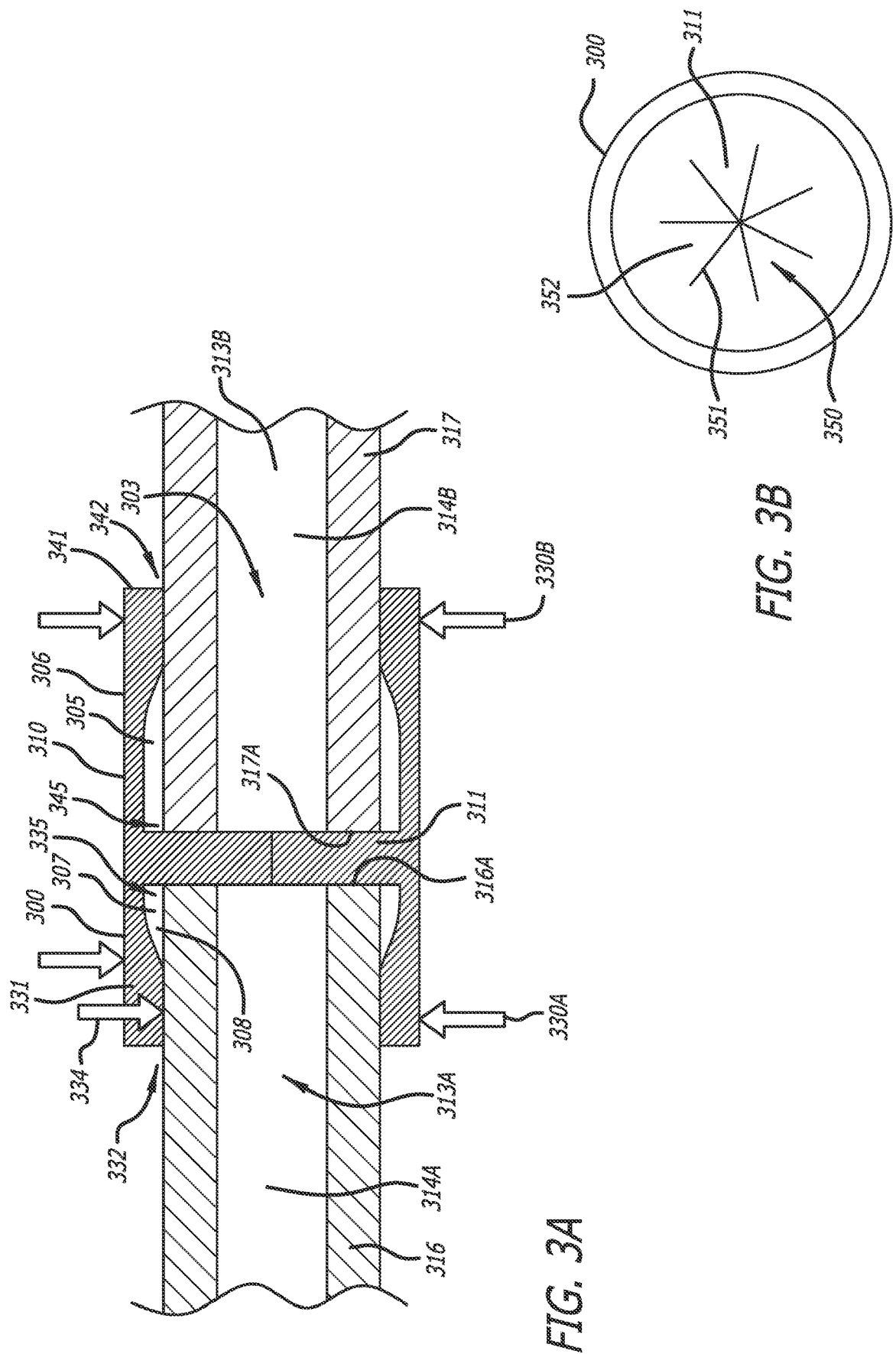

NEGATIVE PRESSURE CONNECTOR SEAL

PRIORITY

This application claims the benefit of priority to U.S. Provisional Application No. 63/219,247, filed Jul. 7, 2021, which is incorporated by reference in its entirety into this application.

BACKGROUND

Targeted temperature management (TTM) systems circulate a fluid (e.g., water) between one or more thermal contact pads coupled to a patient and a TTM fluid control module via a fluid deliver line (FDL). Fluid connectors between the FDL and the pads and between the FDL and the control module provide for the selective connecting and disconnecting of the components. As a clinician may connect and disconnect the components for each TTM procedure (potentially several times per day), it is desirable for the connection to be simple, straight forward, and require minimal forces. It is also important for the fluid seal between the connectors to be reliable.

To prevent water leakage from the TTM system, the system may be configured to operate under a negative pressure so that, in the case of a leaking connection, air may leak into the system as opposed as to water leaking from the system. Disclosed herein are embodiments of devices and methods for utilizing negative internal pressure to improve connector seal reliability while minimizing clinician applied forces to make the connection.

SUMMARY OF THE INVENTION

Briefly summarized, disclosed herein is a sealing member for providing a seal between fluid connectors. The sealing member includes a tubular member defining a lumen extending between a first end and a second end. The tubular member is configured to receive a first connector via the first end and a second connector via the second end. The tubular member includes an annular wall extending between a first annular portion adjacent the first end and a second annular portion adjacent the second end. The first annular portion is configured to engage the first connector and the second annular portion is configured to engage the second connector. When a pressure within the lumen is negative, atmospheric acting inward on the annular wall compresses the sealing member to define a contact force between the second annular portion and the second connector sufficient to define a fluid seal between the sealing member and the second connector.

The pressure within the lumen is defined in response to a fluid pressure within a lumen extending through the first and second connectors and the lumen may be in fluid communication with the lumen extending through the first and second connectors.

In some embodiments, when the pressure within the lumen is negative, atmospheric acting on the annular wall compresses the sealing member to define a contact force between the first annular portion and the first connector sufficient to define a fluid seal between the sealing member and the first connector.

In some embodiments, the first annular portion is attached to the first connector and may also be sealably attached to the first connector. The second annular portion is configured to slidably engage the second connector when a non-negative pressure is defined within the lumen.

One of the first connector or the second connector may be attached to one of a fluid delivery line or a thermal contact pad of a targeted temperature management system, and the other one of the first connector or the second connector may be attached to the other one of the fluid delivery line or a thermal contact pad. The fluid pressure may be defined in accordance with operation of the targeted temperature management system.

The sealing member may further include a septum extending across the lumen between the first connector and the second connector, and the septum includes a pressure actuated valve. The valve is configured to (i) prevent fluid flow through the septum when a fluid pressure across the septum is below a defined pressure limit, and (ii) allow fluid flow through the septum when the fluid pressure across the septum exceeds the defined pressure limit.

Also disclosed herein is a fluid connector system, including a first connector, a complementary second connector fluidly coupled with the first connector, and a tubular sealing member defining a lumen extending between a first end and a second end. The tubular member is configured to receive the first connector via the first end and the second connector via the second end. The tubular member includes an annular wall extending between a first annular portion adjacent the first end and a second annular portion adjacent the second end. The first annular portion is configured to engage the first connector and the second annular portion is configured to engage the second connector. When a pressure within the lumen is negative, atmospheric acting on the annular wall compresses the sealing member to define a contact force between the second annular portion and the second connector sufficient to define a fluid seal between the sealing member and the second connector.

The pressure within the lumen is defined in response to a fluid pressure within a lumen extending through the first and second connectors and the lumen may be in fluid communication with the lumen extending through the first and second connectors.

In some embodiments, when the pressure within the lumen is negative, atmospheric acting on the annular wall compresses the sealing member to define a contact force between the first annular portion and the first connector sufficient to define a fluid seal between the sealing member and the first connector.

In some embodiments, the first annular portion is attached to the first connector and may also be sealably attached to the first connector. The second annular portion is configured to slidably engage the second connector when a non-negative pressure is defined within the lumen.

In some embodiments, the second connector includes a first annular connector wall and a second annular connector wall spaced radially outward of the first annular connector wall. A lateral bottom wall extends between the first and second annular connector walls to define an annular cavity, and the second annular portion is disposed within the annular cavity.

An inside surface of the second annular portion is configured to slidably engage the first annular connector wall, and an outside surface of the second annular portion is configured to slidably and sealably engage the second annular connector wall. When a negative pressure is defined within the lumen, a fluid seal is defined between the inside surface of the second annular portion and the first annular connector wall, and when a non-negative pressure is defined within the lumen, a fluid seal is defined between the outside surface of the second annular portion and the second annular connector wall.

One of the first connector or the second connector may be attached to a component of a targeted temperature management (TTM) system, and the component may be one of a TTM module, a fluid delivery line, or thermal contact pad. The fluid pressure may be defined in accordance with operation of the targeted temperature management system.

The sealing member may include a septum extending across the lumen between the first connector and the second connector, and the septum includes a pressure actuated valve. The valve configured to prevent fluid flow through the septum when a fluid pressure across the septum is below a defined pressure limit, and allow fluid flow through the septum when the fluid pressure across the septum exceeds the defined pressure limit.

Also disclosed herein is a method of defining a seal between fluid connectors. The method includes (i) providing a tubular sealing member defining a lumen extending between a first end and a second end, (ii) inserting a first connector into the sealing member via the first end to define a first engagement, (iii) inserting a second connector into the sealing member via the second end to define a second engagement, (iv) establishing a negative pressure within the lumen to transition the sealing member from a first engagement configuration to a second engagement configuration. In the first engagement configuration, at least one of the first connector or the second connector is not sealably coupled with the sealing member, and in the second engagement configuration, atmospheric pressure compresses the sealing member to define a fluid seal between the least one of the first connector or the second connector and the sealing member. In the second engagement configuration, separation of the second connector from the first connector may be prevented.

The method may further include (i) establishing a non-negative pressure within the lumen to transition the sealing member from the second engagement configuration to the first engagement configuration and (ii) separating the second connector from the first connector.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 3A illustrates a side cross-sectional view of a third embodiment of the sealing member, in accordance with some embodiments.

FIG. 3B illustrates a septum of the sealing member of FIG. 3A, in accordance with some embodiments.

DETAILED DESCRIPTION

Figure 1:
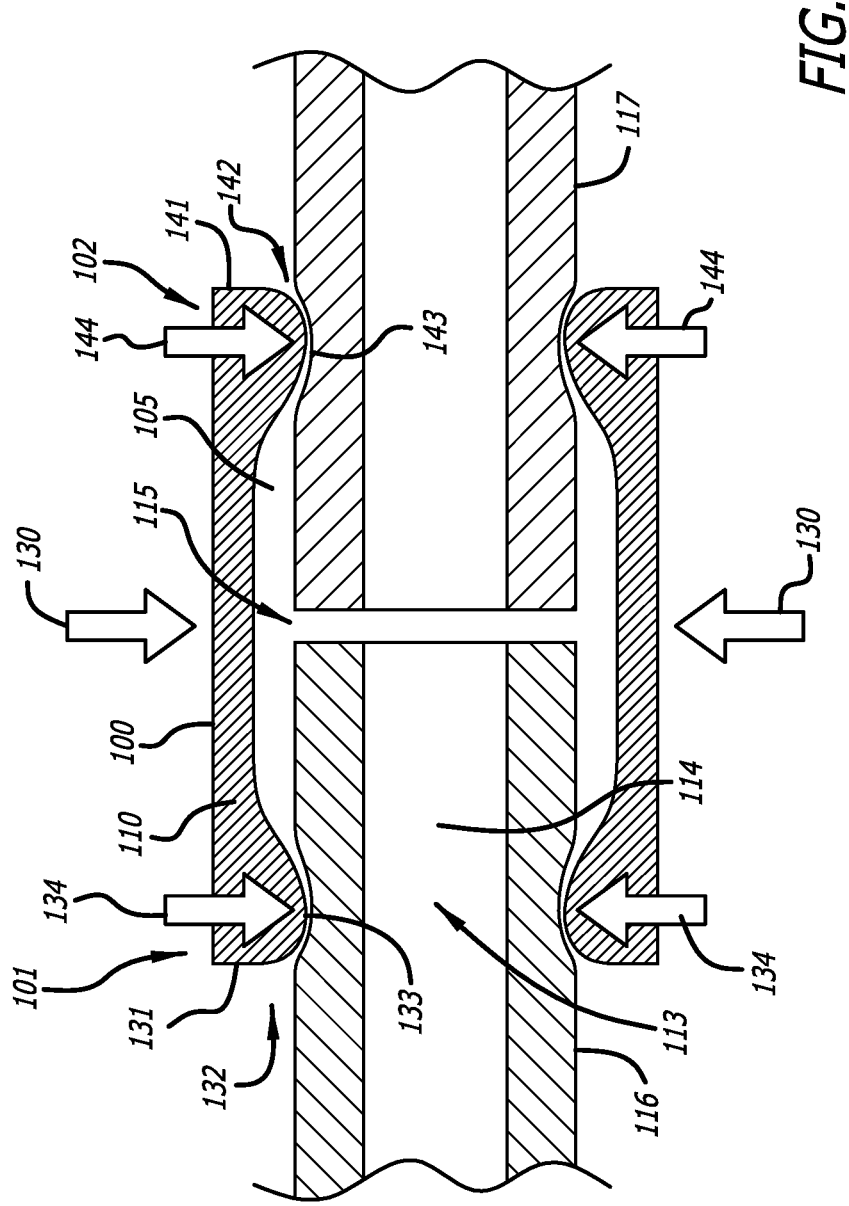
FIG. 1 illustrates a side cross-sectional view of a sealing member for providing a fluid seal between connectors, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising." Furthermore, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The phrases "connected to" and "coupled to" refer to any form of interaction between two or more entities, including mechanical, electrical, magnetic, electromagnetic, fluid, signal, communicative (including wireless), and thermal interaction. Two components may be connected or coupled to each other even though they are not in direct contact with each other. For example, two components may be coupled to each other through an intermediate component.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Unless defined otherwise, all technical and scientific terms used herein have the same meaning as commonly understood by those of ordinary skill in the art.

FIG. 1 illustrates a cross-sectional side view of a sealing member 100 coupled between representative fluid connectors, i.e., the first connector 116 and the second connect 117, in a connected state. A fluid lumen 113 extends longitudinally through the connectors 116, 117. The sealing member 100 is configured to provide a fluid seal between the first and second connectors 116, 117. In some embodiments, the sealing member 100 may define a primary seal between the connectors. In other embodiments, the sealing member 100 may define a secondary seal (i.e., a backup seal) between the first and second connectors 116, 117.

In some embodiments, the first and second connectors 116, 117 may be attached to components of a TTM system (not shown). For example, the first and second connectors 116, 117 may define a fluid connection between a fluid delivery line and a thermal pad. In another example, the first and second connectors 116, 117 may define a fluid connection between a fluid delivery line and a TTM module.

The sealing member 100 may generally define a tubular shape having an annular wall 110. The annular wall 110 may extend circumferentially around and longitudinally along each of the connectors 116, 117. The sealing member 100 may be positioned with respect to the connectors 116, 117 so that a junction point 115 of the connectors 116, 117 is located between a first end 101 and a second end 102 of the sealing member 100.

The sealing member 100 may be an elastic sleeve/shroud configured to deflect or deform in response to externally applied forces. In some embodiments, the sealing member 100 may include one or more deflectable/deformable portions. The sealing member 100 or at least a portion thereof may be formed of a flexible/deformable material such as silicone, ethylene propylene diene monomer rubber (EPDM), a natural rubber, or any other suitably flexible material. In some embodiments, the sealing member 100 may include supporting structural elements, such as a coil, longitudinal stiffening wires, circular rings, or any other structure elements consistent with the functionality of the sealing member 100.

The sealing member 100 may be attached to the first connector 116 to inhibit or prevent longitudinal displacement of the sealing member 100 with respect to the first connector 116. In some embodiments, rotation of the sealing member 100 with respect to the first connector 116 may also be inhibited. The attachment of the sealing member 100 to the first connector 116 may define a fluid seal 132 between sealing member 100 and the first connector 116.

The sealing member 100 may be coupled with the first connector 116 via a contact force between the sealing member 100 and the first connector 116. For example, a first engagement portion 131 of the sealing member 100 may be sized to fit within a recess 133 of the first connector 116 while defining an interference fit with the first connector 116. In some embodiments, the sealing member 100 may include a separate device (e.g., a band clamp, not shown) to define the contact force. In other embodiments, the sealing member 100 may be bonded to the first connector 116 via an adhesive. The coupling of the first engagement portion 131 with the first connector 116 may define the fluid seal 132 between the sealing member 100 and the first connector 116. By way of summary, the sealing member 100 may be permanently attached to the first connector 116 or selectively attached to and/or detached from the first connector 116.

The sealing member 100 engages the second connector 117 via a second engagement portion 141. The second engagement portion 141 is sized to fit within a recess 143 defining an interference fit with the second connector 117. The interference fit is defined to accommodate longitudinal displacement of the second connector 117 relative to sealing member 100. In other words, a contact force 144 between the second engagement portion 141 and second connector 117 may be sufficiently minimal to allow the second connector 117 to be inserted into and extracted from the sealing member 100 manually be a clinician while also defining a seal 142 between the sealing member 100 and the second connector 117.

The sealing member 100 defines an annular chamber 105 (e.g., annular space or gap) between the connectors 116, 117 and the annular wall 110. The chamber 105 is bounded on the ends by the engagement portions 131, 141. The chamber 105 may be in fluid communication with the lumen 113 via a leak path between the connectors 116, 117 at the junction point 115. As such, the fluid pressure 114 within the lumen 113 may define a chamber pressure 106 of the chamber 105. In an instance of a negative pressure within the lumen 113, the resulting negative chamber pressure 106 causes atmospheric pressure to exert a radially inward force 130 on the annular wall 110. In such an instance, the radially inward force 130 causes an increase in the contact force 144 between the second engagement portion 141 and the second connector 117. The seal 142 between the second engagement portion 141 and the second connector 117 may be enhanced by the increase in the contact force 144 resulting from the negative chamber pressure 106.

In some embodiments, the radially inward force 130 applied to the annular wall 110 may also increase a contact force 134 between the first engagement portion 131 and the first connector 10. Consequently, the negative pressure 114 with the lumen 113 may define a greater integrity of the seal 132.

The sealing member 100 is configured to engage the second connector 117 according to a first engagement configuration and a second engagement configuration as defined by the pressure 114 within the lumen 113. More specifically, the sealing member 100 may be disposed in a first engagement configuration when the pressure 114 is non-negative. The sealing member 100 may transition toward the second engagement configuration in response to a negative pressure 114. In the first engagement configuration, the sealing member 100 may facilitate coupling and decoupling of the connectors 116, 117. As such, longitudinal and/or rotational displacement between the sealing member 100 and the second connector 117 is allowed in the first engagement configuration.

The second engagement configuration defines enhanced engagement properties over the first engagement configuration. The second engagement configuration defines a greater integrity of the seal 142 than the first engagement configuration. Similarly, the second engagement configuration may define a greater frictional force between the sealing member 100 and the second connector 117 resisting longitudinal and rotational displacement of the second connector 117 with respect to the sealing member 100.

In use, the sealing member 100 may automatically transition between the first engagement configuration and the second engagement configuration. In some embodiments, the sealing member 100 may transition from the second engagement configuration to the first engagement configuration to facilitate connection and/or disconnection of the connectors 116, 117. Similarly, the sealing member 100 may transition from the first engagement configuration to the second engagement configuration to establish the seal 142 only when the first connector 116 is coupled with the second connector 117. Additionally, the sealing member 100 may transition from the first engagement configuration to the second engagement configuration in response to a change the pressure 116 toward the negative and in some embodiments, the negative pressure may be defined by the TTM module.

A method of using the sealing member 100 may include the following steps or processes. The sealing member 100 is coupled with the first connector. The first connector 116 is coupled with the second connector 117 during which the second connector 117 is inserted within the sealing member 117. A negative pressure is established within the lumen 113. In the event of a leak between the connectors 116, 117, the negative causes the sealing member 100 to form a seal 142 between the sealing member 100 and the second connector 117. In some embodiments, the vacuum also causes the sealing member 100 to form a seal 132 between the sealing member 100 and the first connector 116. The negative is released from the lumen 113 and the second connector 117 is separated from the first connector 116 during which the second connector is withdrawn from the sealing member 100.

Figure 2:
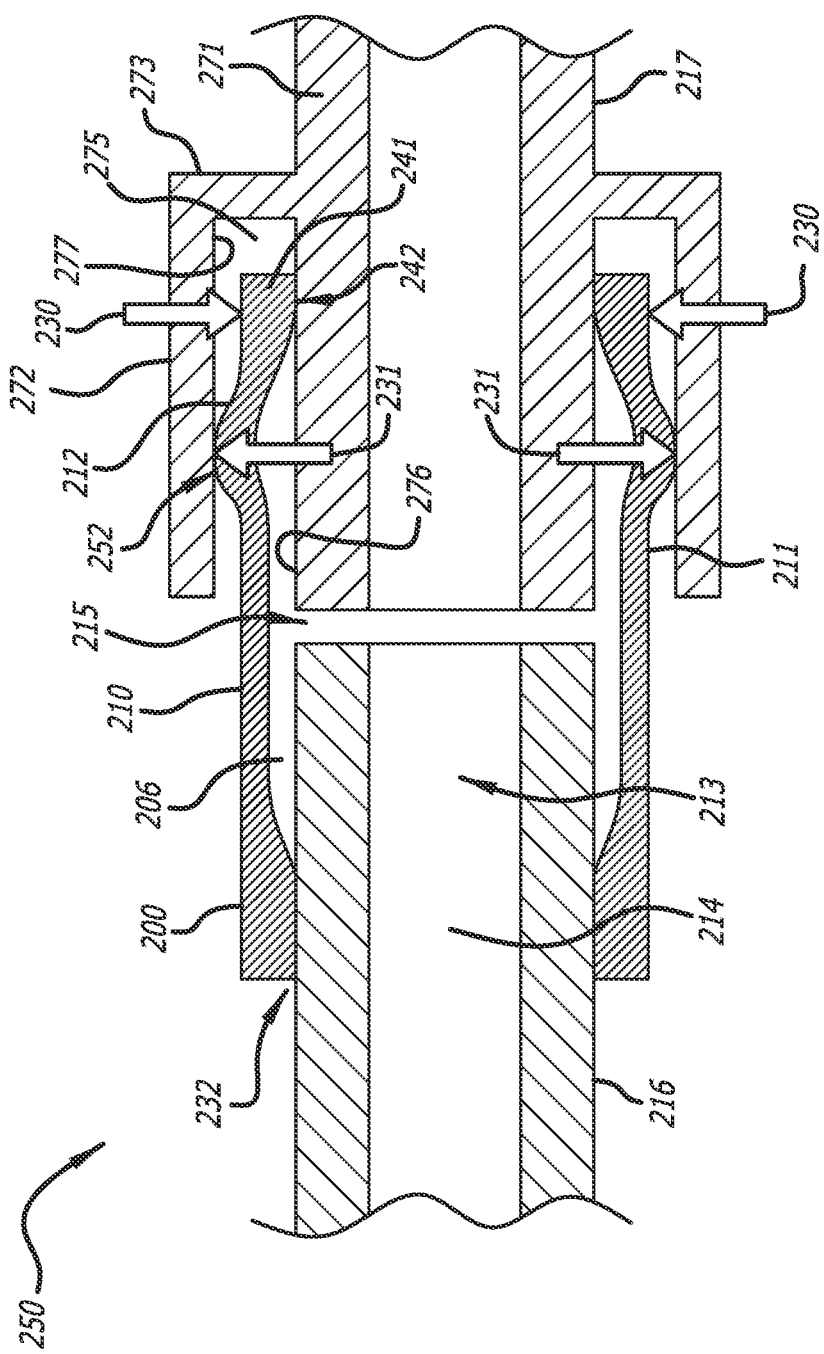
FIG. 2 illustrates a side cross-sectional view of a connector system including a second embodiment of the sealing member, in accordance with some embodiments.

FIG. 2 illustrates a connector system 250 in a connected state. The connector system 250 generally includes a first connector 216, a complementary second connector 217, and sealing member 200. The sealing member 200 can, in certain respects, resemble components of the sealing member 100 described in connection with FIG. 1. It will be appreciated that all the illustrated embodiments may have analogous features. Accordingly, like features are designated with like reference numerals, with the leading digits increment to "2." For instance, the annular wall is designated as "110" in FIG. 1, and an analogous annular wall is designated as "210" in FIG. 2. Relevant disclosure set forth above regarding similarly identified features thus may not be repeated hereafter. Moreover, specific features of the sealing member 100 and related components shown in FIG. 1 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the sealing member 200. Any suitable combination of the features, and variations of the same, described with respect to the sealing member 100 and components illustrated in FIG. 1 can be employed with the sealing member 200 and components of FIG. 2, and vice versa. This pattern of disclosure applies equally to further embodiments depicted in subsequent figures and described hereafter.

The sealing member 200 is sealably attached to a first connector 216. The second connector 217 includes an inner annular wall 271 defining the lumen of the second connect 217. The second connector 217 further includes an outer annular wall 272 spaced radially away from the inner annular wall 271. A bottom wall 273 extends between the inner wall 271 and the outer wall 272 to define an annular cavity 275 (i.e., a receiving moat). The cavity 275 includes an inner sealing surface 276 and an outer sealing surface 277.

As shown in FIG. 2, when the connectors 216, 217 are coupled together, an extending portion 211 (i.e., an elastomeric sleeve) of the sealing member 210 is inserted within the cavity 275. When inserted, an expanded portion 212 of the sealing member 210 is disposed adjacent the outer sealing surface 277. The expanded portion 212 is sized to sealably contact the outer sealing surface 277. In other words, in the free state (i.e., absent any external forces), an outside diameter defined by the expanded portion 212 is greater than an inside diameter defined by the outer sealing surface 277. Consequently, upon coupling of the connectors 216, 217, the expanded portion 212 is compressed (i.e., forced radially inward) by the outer sealing surface 277 defining a seal 252 between the expanded portion 212 and the outer sealing surface 277 or more generally, between the sealing member 200 and the second connector 217.

In similar fashion to the sealing member 100 described above, the sealing member 200 may transition between a first engagement configuration and second engagement configuration in accordance with a change of fluid pressure 214 within the lumen 213. In the first engagement configuration, consistent with a positive/zero fluid pressure 214, the seal 252 is established between the sealing member 200 and the second connector 217. In the second engagement configuration, consistent with a negative fluid pressure 214, the seal 242 is established or enhanced between the sealing member 200 and the second connector 217.

In use, the seal 252 prevents leakage of water from the junction point 215 when a positive/zero pressure 214 is present within the lumen 213. More specifically, a positive/zero pressure 214 translates to the positive/zero chamber pressure 206 within the chamber 205 allowing the expanded portion 212 to define a contact force 231 against the outer sealing surface 277. The radially outward force 231 causes the expanded portion 212 to form the seal 252 with the outer sealing surface 277.

Similarly, air leakage into the lumen 213 is prevented by the seal 242 when a negative fluid pressure 214 is present within the lumen 213. More specifically, the negative fluid pressure 214 translates to a negative chamber pressure 206 causing the atmospheric pressure to exert a radially inward force 230 on the annular wall 210. The radially inward force causes the engagement portion 241 to form the seal 242 with the inner sealing surface 276.

A method of using the sealing member 200 may include forming the seal 252 between the sealing member 200 and the second connector 217 upon coupling of the second connector 217 with the first connector 216.

FIG. 3A illustrates a sealing member 300 in use with a first connector 316 and second connector 317. The sealing member 300 may generally define a tubular shape defining a sealing member lumen 303. The sealing member 300 includes an annular wall 310 and a septum wall 311 extending across the sealing member lumen 303. The annular wall 310 may extend circumferentially around and longitudinally along each of the connectors 316, 317. The sealing member 300 may be positioned with respect to the connectors 316, 317 so that the ends 316A, 317A of the connector 316, 317 are disposed adjacent the septum wall 311.

The sealing member 300 engages the second connector 317 via a second engagement portion 341. The second engagement portion 341 is sized to define a sliding fit between the sealing member 300 and the second connector 317. In other words, a contact force 344 between the second engagement portion 341 and second connector 317 may be sufficiently minimal to allow the second connector 317 to be inserted into and extracted from the sealing member 300.

The sealing member 300 defines an annular chamber 307 (e.g., annular space or gap) between the first connector 316 and the annular wall 310. The chamber 307 is bounded on the ends by the septum wall 311 and the first engagement portion 331. The chamber 307 may be in fluid communication with the lumen 313A via a leak path between the first connector 316 and the septum wall 311. As such, the fluid pressure 314A within the lumen 313A may define a chamber pressure 308 of the chamber 307. In an instance of a negative fluid pressure 314A within the lumen 313A, the resulting negative chamber pressure 308 causes atmospheric pressure to exert a radially inward force 330A on the annular wall 310. In such an instance, the radially inward force 330A causes an increase in the contact force 334 between the first engagement portion 331 and the first connector 316. A seal 332 between the first engagement portion 331 and the first connector 316 may be defined by the contact force 334 resulting from the negative chamber pressure 308.

Similarly, the sealing member 300 defines an annular chamber 305 (e.g., annular space or gap) between the second connector 317 and the annular wall 310. The chamber 305 is bounded on the ends by the septum wall 311 and the second engagement portion 341. The chamber 305 may be in fluid communication with the lumen 313B via a leak path between the second connector 317 and the septum wall 311. As such, the fluid pressure 314B within the lumen 313B may define a chamber pressure 306 of the chamber 305. In an instance of a negative fluid pressure 314B within the lumen 313B, the resulting negative chamber pressure 306 causes atmospheric pressure to exert a radially inward force 330B on the annular wall 310. In such an instance, the radially inward force 330B causes an increase in the contact force 344 between the second engagement portion 341 and the second connector 317. A seal 342 between the second engagement portion 341 and the second connector 317 may be defined by the contact force 344 resulting from the negative chamber pressure 306.

The sealing member 300 may be attached to the first connector 316 to inhibit or prevent longitudinal displacement of the sealing member 300 with respect to the first connector 316. In some embodiments, rotation of the sealing member 300 with respect to the first connector 316 may also be inhibited. The attachment of the sealing member 300 to the first connector 316 may define a fluid seal between sealing member 300 and the first connector 316. In other embodiments, the sealing member 300 may include a separate device (e.g., a band clamp, not shown) to define the contact force. In other embodiments, the sealing member 300 may be bonded to the first connector 316 via an adhesive. The sealing member 300 may be permanently attached to the first connector 316 or selectively attached to and/or detached from the first connector 316.

The sealing member 300 is configured to engage the second connector 317 according to a first engagement configuration and a second engagement configuration as defined by a pressure within the lumen 313B. More specifically, the sealing member 300 may be disposed in a first engagement configuration when the pressure 314B is non-negative. The sealing member 300 may transition toward the second engagement configuration in response to a pressure 314B that is negative. In the first engagement configuration, the sealing member 300 may facilitate coupling and decoupling of the connectors 316, 317. As such, longitudinal and/or rotational displacement between the sealing member 300 and the second connector 317 is allowed in the first engagement configuration.

The second engagement configuration may define enhanced engagement properties over the first engagement configuration. In some embodiments, the second engagement configuration may define a greater integrity of the seal 342 than the first engagement configuration. Similarly, the second engagement configuration may define a greater frictional force between the sealing member 300 and the second connector 317 resisting longitudinal and rotational displacement of the second connector 317 with respect to the sealing member 300.

In some embodiments, the septum wall 311 defines a face seal 335 with the end 316A of the first connector 316. The septum wall 311 may also define a face seal 345 with the end 317A of the second connector 317. As such the septum wall 311 may define a fluid seal between the connectors 316, 317.

FIG. 3B is an end view of the sealing member 300. The septum wall 311 includes one or more slits 351 extending through the septum wall 311. The slits 351 along with the corresponding elastomeric flaps 352 define a pressure actuated star valve 350. The slits 351 and flaps 352 are configured to define a septum seal in the absence of a pressure difference across the septum 311. More specifically, when the pressure difference across the septum 311 is below a defined limit, the star valve 350 is in a closed state preventing fluid flow through the sealing member 300. Conversely, when the pressure difference across the septum 311 exceeds the defined limit, the flaps 352 deflect to transition the star valve 350 to an open state allowing fluid flow through the sealing member 300.

In use, deliberate fluid flow (e.g., flow caused by a pump) through the connectors 316, 317 produces a pressure difference across the septum 311 causing the star valve 350 to open. When the fluid flow is stopped, the pressure difference is eliminated allowing the star valve 350 to close. In further use, the sealing member 300 may be attached to the first connector 316 so that when deliberate fluid flow is stopped and the connectors 316, 317 are separated, the sealing member 300 remains coupled with the first connector 316 preventing inadvertent fluid flow out of the first connector 316.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A sealing member for providing a seal between fluid connectors, comprising:
a tubular member defining a lumen extending between a first end and a second end, the tubular member configured to receive a first connector via the first end and a second connector via the second end, the tubular member comprising an annular wall defining:
a first annular portion adjacent the first end, the first annular portion configured to engage the first connector;
a second annular portion adjacent the second end, the second annular portion configured to engage the second connector; and
an annular chamber extending between the first annular portion and the second annular portion, the annular chamber configured to receive the first connector and the second connector therein;

wherein during use:
the first connector and the second connector extend into the annular chamber such that the annular chamber defines an annular space between the annular wall and each of the first connector and the second connector,
the annular chamber adjacent the first annular portion is in fluid communication with the annular chamber adjacent the second annular portion, and
when a pressure within the lumen is negative, atmospheric pressure acting on the annular wall compresses the tubular member to define at least a contact force between the second annular portion and the second connector sufficient to define a fluid seal between the tubular member and the second connector.

2. The sealing member of claim 1, wherein the pressure within the lumen is defined in response to a fluid pressure within a fluid lumen extending through the first connector and the second connector.

3. The sealing member of claim 2, wherein the lumen is in fluid communication with the fluid lumen.

4. The sealing member of claim 1, wherein when the pressure within the lumen is negative, the atmospheric pressure acting on the annular wall compresses the tubular member to define the contact force between the first annular portion and the first connector sufficient to define the fluid seal between the tubular member and the first connector.

5. The sealing member of claim 1, wherein the first annular portion is configured to attach to the first connector.

6. The sealing member of claim 1, wherein the first annular portion is configured to sealably attach to the first connector.

7. The sealing member of claim 1, wherein the second annular portion is configured to slidably engage the second connector when a non-negative pressure is defined within the lumen.

8. The sealing member of claim 1, further comprising a septum extending across the lumen between the first annular portion and the second annular portion, the septum including a pressure actuated valve configured to:
prevent fluid flow through the septum when a fluid pressure across the septum is below a defined pressure limit, and
allow fluid flow through the septum when the fluid pressure across the septum exceeds the defined pressure limit.

9. A fluid connector system, comprising:
a first connector;
a complementary second connector fluidly coupled with the first connector; and
a tubular sealing member defining a lumen extending between a first end and a second end, the tubular sealing member configured to receive the first connector via the first end and a second connector via the second end, the tubular sealing member, comprising an annular wall defining:
a first annular portion adjacent the first end, the first annular portion configured to engage the first connector;
a second annular portion adjacent the second end, the second annular portion configured to engage the second connector; and
an annular chamber extending between the first annular portion and the second annular portion, the annular chamber configured to receive the first connector and the second connector therein;

wherein during use:
the first connector and the second connector extend into the annular chamber such that the annular chamber defines an annular space between the annular wall and each of the first connector and the second connector,
the annular chamber adjacent the first annular portion is in fluid communication with the annular chamber adjacent the second annular portion, and
when a pressure within the lumen is negative, atmospheric pressure acting on the annular wall compresses the tubular sealing member to define at least a contact force between the second annular portion and the second connector sufficient to define a fluid seal between the tubular sealing member and the second connector.

10. The fluid connector system of claim 9, wherein the pressure within the lumen is defined in response to a fluid pressure within a fluid lumen extending through the first connector and the second connector.

11. The fluid connector system of claim 10, wherein the lumen is in fluid communication with the fluid lumen.

12. The fluid connector system of claim 9, wherein when the pressure within the lumen is negative, the atmospheric pressure acting on the annular wall compresses the tubular sealing member to define a contact force between the first annular portion and the first connector sufficient to define a fluid seal between the tubular sealing member and the first connector.

13. The fluid connector system of claim 9, wherein the first annular portion is attached to the first connector.

14. The fluid connector system of claim 9, wherein the first annular portion is sealably attached to the first connector.

15. The fluid connector system of claim 9, wherein the second annular portion is configured to slidably engage the second connector when a non-negative pressure is defined within the lumen.

16. The fluid connector system of claim 9, wherein the second connector comprises:
a first annular connector wall;
a second annular connector wall spaced radially outward of the first annular connector wall; and
a lateral bottom wall extending between the first annular connector wall and the second annular connector wall, wherein the first annular connector wall, the second annular connector wall, and the lateral bottom wall define an annular cavity, and
the second annular portion is disposed within the annular cavity.

17. The fluid connector system of claim 16, wherein:
an inside surface of the second annular portion is configured to slidably engage the first annular connector wall, and
an outside surface of the second annular portion is configured to slidably and sealably engage the second annular connector wall.

18. The fluid connector system of claim 16, wherein:
when a negative pressure is defined within the lumen, a fluid seal is defined between an inside surface of the second annular portion and the first annular connector wall, and when a non-negative pressure is defined within the lumen, a fluid seal is defined between an outside surface of the second annular portion and the second annular connector wall.

19. The fluid connector system of claim 9, wherein:
one of the first connector or the second connector is attached to a component of a targeted temperature management (TTM) system, and
the component is one of a TTM module, a fluid delivery line, or a thermal contact pad.

20. The fluid connector system of claim 19, wherein a fluid pressure is defined in accordance with operation of the targeted temperature management system.

21. The fluid connector system of claim 9, wherein the tubular sealing member includes a septum extending across the lumen between the first connector and the second connector, the septum including a pressure actuated valve configured to:
prevent fluid flow through the septum when a fluid pressure across the septum is below a defined pressure limit, and
allow fluid flow through the septum when the fluid pressure across the septum exceeds the defined pressure limit.

22. A method of defining a seal between fluid connectors, comprising:
providing a tubular sealing member defining a lumen extending between a first end and a second end;
inserting a first connector into the tubular sealing member via the first end to define a first engagement;
inserting a second connector into the tubular sealing member via the second end to define a second engagement;
establishing a negative pressure within the lumen to transition the tubular sealing member from a first engagement configuration to a second engagement configuration, wherein:
in the first engagement configuration, at least one of the first connector or the second connector is not sealably coupled with the tubular sealing member, and
in the second engagement configuration, atmospheric pressure compresses the tubular sealing member to define a fluid seal between the at least one of the first connector or the second connector and the tubular sealing member.

23. The method of claim 22, wherein in the second engagement configuration, separation of the second connector from the first connector is prevented.

24. The method of claim 22, further comprising:
establishing a non-negative pressure within the lumen to transition the tubular sealing member from the second engagement configuration to the first engagement configuration; and
separating the second connector from the first connector.

* * * * *